United States Patent
Cywinski (10) Patent No.: US 8,175,713 B1
(45) Date of Patent: May 8, 2012

(54) ELECTRO-STIMULATION DEVICE TO PUMP BLOOD FROM LEGS

(76) Inventor: Jozef Cywinski, Orsieres (CH)

( * ) Notice: Subject to any disclaimer, the term of this patent is extended or adjusted under 35 U.S.C. 154(b) by 852 days.

(21) Appl. No.: 11/621,941

(22) Filed: Jan. 10, 2007

(51) Int. Cl.
*A61N 1/18* (2006.01)

(52) U.S. Cl. .................. 607/48; 607/49; 607/72

(58) Field of Classification Search ............. 607/48, 607/2, 3, 65, 72, 49
See application file for complete search history.

(56) References Cited

U.S. PATENT DOCUMENTS

| | | |
|---|---|---|
| 1,908,688 A | 5/1933 | Call |
| 2,375,575 A | 5/1945 | Moreland et al. |
| 3,083,712 A | 4/1963 | Keegan, Jr. |
| 3,516,413 A | 6/1970 | McDonald et al. |
| 4,528,984 A | 7/1985 | Morawetz et al. |
| RE32,091 E | 3/1986 | Stanton |
| 4,712,558 A | 12/1987 | Kidd et al. |
| 5,048,522 A | 9/1991 | Petrofsky |
| 5,350,415 A | 9/1994 | Cywinski |
| 5,620,463 A * | 4/1997 | Drolet ............................ 607/3 |
| 6,226,552 B1 * | 5/2001 | Staunton et al. ............. 607/72 |
| 6,701,189 B2 | 3/2004 | Fang et al. |
| 2002/0188331 A1 | 12/2002 | Fang et al. |
| 2004/0267333 A1 * | 12/2004 | Kronberg .................... 607/72 |
| 2008/0132962 A1 * | 6/2008 | DiUbaldi et al. .............. 607/2 |

FOREIGN PATENT DOCUMENTS

| | | |
|---|---|---|
| EP | 0.459.945 | 11/1991 |
| GB | 2.085.733 | 5/1982 |
| WO | WO95/33516 | 12/1995 |

* cited by examiner

*Primary Examiner* — Niketa Patel
*Assistant Examiner* — Rex R Holmes
(74) *Attorney, Agent, or Firm* — Michael I. Kroll (57) ABSTRACT

A device for providing electric stimulation for treatment of medical and non-medical conditions connected with blood circulation in legs. The device includes means for generating a shaped electrical impulse according to a pre-stored timing pattern. A means for conditioning the shaped impulse is coupled to said generating means and means for applying the conditioned shaped impulse to a user for causing a deep and painless contraction of a user's calf muscles, which in turn activate blood circulation and improve venous return from legs.

15 Claims, 7 Drawing Sheets

ELECTRO-STIMULATION DEVICE TO PUMP BLOOD FROM LEGS

BACKGROUND OF THE INVENTION

1. Field of the Invention

The present invention relates generally to medical treatment apparatus and more specifically to a method and apparatus that provides muscle-assisted pumping of venous blood from legs. The purpose of this apparatus and method is to prevent a medical condition called deep venous thrombosis (DVT) and also to reduce and/or to prevent leg and ankle swelling in persons who are motionless while standing or sitting for extended periods of time. This concerns, for example, travelers on long haul flights or in cars, computer operators, salespersons, etc.

The method and the device as described in the present invention utilize electrically stimulated calf muscles in legs. The stimulation causes rhythmical contractions of muscles in both calves, which in turn squeeze out venous blood from intramuscular veins and deep central veins in legs. This results in forced venous blood flow from legs upwards against gravity in the direction of lungs and heart. This is augmented by the action of valves inside the veins which prevent the return of squeezed blood volume back into leg veins.

To obtain such rhythmical and effective muscle contractions, a special kind of electrical neuromuscular stimulation device is used. Such device and method of its application for the above purpose is the subject of this instant invention.

The present invention of stimulation method and device thereof utilizes a continuous train of very short electrical impulses at a predetermined durational range and frequency wherein, superimposed on top of this continuous train of electrical impulses, there are rhythmic (cyclic) periods of modulated bursts of energy associated therewith. The timing of these bursts of energy approximates or is close to a heart rate and the electrical stimulation is delivered by means of two electrodes while only one stimulating electrode is applied to a skin of each leg.

2. Description of the Prior Art

Numerous Electro-stimulation Devices have been provided in prior art. For example, U.S. Pat. Nos. 1,908,688, Re. 32091, 6,701,189, 2,375,575, 4,712,558, 3,083,712, 5,048,522, 3,516,413, 5,350,415, U.S. Patent application No. 2002/188331, U.K. Patent No. GB2085733, PCT Patent Application WO 95/33516 to Pick et al., all are illustrative of such prior art.

There are three known muscle stimulation devices and methods; they are low frequency stimulators, high frequency interferential stimulators and Russian-Current stimulators. These three basic types have their respective advantages and disadvantages, but none of them can provide stimulation with optimal effectiveness and safety combined with the ease of use. In addition the pain usually compromises their effectiveness, when electricity is applied over the skin. Furthermore, they are neither easy nor practical to use, as they usually require applying at least two and up to six electrodes and associated connecting cables for each stimulated muscle.

The most common of commercially available muscle stimulators are so-called "LOW FREQUENCY" electrical stimulators. They are used both in medical field and non-medical applications. Many are battery powered and some of them are suitable for individual use at home. Their utilization is broad, ranging from rehabilitation, sport medicine, aid to athletic training, body building and shaping, to slimming, anti-cellulite and beauty applications. They are inexpensive, not always easy to use and are marginally effective and uncomfortable. These LOW FREQUENCY stimulators can deliver electrical impulses in various time sequences. The time sequences, frequencies and other impulse parameters are usually controlled by the health professional or by the users themselves. These impulses are delivered to motor points on the user's skin via electrically conductive pads. This results in muscle contractions that are either too weak and too superficial to be effective. The user of these LOW FREQUENCY stimulators may also incur a pain during tetanic muscular contractions which further limits the effectiveness of these LOW-FREQUENCY stimulators. For the stimulation to be effective it must produce many maximally strong but painless contractions, at a level preferably close to that of MVC (maximal voluntary contraction) force. The most limiting factor for effectiveness of LOW-FREQUENCY stimulators is an increasing pain associated with the increasing intensity of stimulation. Such pain does not usually permit the achievement of high intensity stimulation levels necessary to produce strong muscle contractions. This is due to the shape, frequency and character (waveforms) of the electrical impulses, produced by these stimulators. The quasi-rectangular mono-phase or bi-phase stimulation current waveform are most commonly used impulse shapes in these LOW FREQUENCY stimulators. The time pauses between these impulses, called inter-pulse intervals, are in the range from 0.01 second to 1 second, which respectively correspond to the frequencies of 100 Hz (Hertz) down to 1 Hz, with a most commonly used frequencies around 50 Hz. The impulse durations (widths) commonly used in these stimulators are in a range from 300 to 800 microseconds. Some stimulators in this category include programmed sequences of impulse durations and frequencies stored in their internal electronic memory. The program and execute modes to accomplish storage of frequency and impulse duration parameters by using electronic memory were disclosed by Morales and Burdette in the U.S. Pat. No. 4,528,984.

Unfortunately, the frequency and impulse duration ranges of LOW FREQUENCY stimulators lie within the same range as the maximal sensitivity of the pain receptors in the human skin, which is around 50 Hertz and therefore cause pain in association with tetanic muscle contractions.

The second type of the above mentioned trans-cutaneous muscle stimulators are "HIGH FREQUENCY INTERFERENTIAL" stimulators. They are suitable mostly for clinical use as they require line power and must be applied by health professionals. They are more effective than most domestic LOW FREQUENCY stimulators and are relatively painless, but possess the disadvantage of being unsafe for use by untrained persons. Furthermore, these HIGH FREQUENCY INTERFERENTIAL stimulators are expensive and bulky. They deliver two stimulation waveforms simultaneously in crossway geometric pattern. The waveforms are continuous and sinusoidal in shape and operate in a frequency range from 2000 Hz to 5000 Hz. These waveforms are mixed in the tissues under the skin by so-called interference, which produces a beat frequency in a range very similar to that of the "LOW FREQUENCY" stimulators (1 to 100 Hz). However, their effectiveness is limited by the fact that the trained operator is unaware of the location that the interference beat frequency is produced beneath the skin, thereby making direct targeting treatment difficult.

The third existing type of neuromuscular stimulators, called "RUSSIAN CURRENT" operates also in the same high frequency range as discussed above with respect to the HIGH FREQUENCY INTERFERENTIAL stimulators. However these RUSSIAN CURRENT stimulators do not function using the interference phenomenon. The RUSSIAN CURRENT stimulators produce a single type of stimulation waveform per channel. The Russian Current waveform is usually sinusoidal in shape and it has high frequency oscillations ranging from 2000 Hz to 5000 Hz. This sinusoidal waveform oscillations are interrupted every 0.01 to 0.02 seconds. These stimulators are painful and unsafe for use by untrained persons and are also expensive and bulky.

While all these stimulators may be suitable for the particular purpose to which they address, they would not be as suitable for the purpose of the present invention as heretofore described.

U.S. Pat. No. 1,908,688

Inventor: Lloyd L. Call

Issued: May 16, 1933

This invention relates to apparatus for the generation of currents suitable for use in electro-medical work.

U.S. Pat. No. 2,75,575

Inventor: Preben Morland et al.

Issued: May 8, 1945

The invention relates to an apparatus for treatment of nerves and muscles with electric pulses, for instance for therapeutic and diagnostic purposes.

U.S. Pat. No. 3,083,712

Inventor: James E. Keegan Jr.

Issued: Apr. 2, 1963

This invention relates generally to electrical muscle therapy and more specifically to programmed sequence for muscle therapy.

U.S. Pat. No. 3,516,413

Inventor: Michael Mcdonald et al.

Issued: Jun. 23, 1970

A circuit for an electric muscle stimulator including a surging waveform generator, a square waveform generator, a mixer, and a output stage, in which the outputs in from surging waveform generator and the square waveform generator are applied to the mixer stage in such a way that the output from the square waveform generator provides 100% modulation of the signal output, from the mixing stage.

European Patent Number GB 2085733

Inventor: Amadej Trnkoczy et al.

Issued: May 6, 1982

In a control circuit for a functional and therapeutic stimulator 16 which generates pulses are generated for artificially causing muscle contractions, the amplitude of the pulses and thus the intensity of contractions can be regulated in dependence upon a positional pick-up constituted by a potentiometer 7. The initial part of the movement of the slider of potentiometer 7 away from its zero position causes a transistor 12 to operate a switch 15 thereby connecting stimulator 16 to battery 4. A potentiometer 11 controls the slope of the characteristic of stimulation pulse amplitude plotted against the setting of potentiometer 7. When a switch 3 is positioned with its contacts 20, 24, the stimulator 16 is controlled to give an interrupted pulse train output with ON and Off periods controlled by a generator 14.

U.S. Pat. No. Re. 32,091

Inventor: David J. Stanton

Issued: Mar. 11, 1986

A dual channel neuromuscular stimulator. Pulses developed by a pulse generator are transmitted alternately on both channels to involuntarily contract muscles. The stimulator has variable on/off cycling capability to provide flexibility in meeting the stimulation needs of patients and has output current adjustments and other variable parameter settings to achieve optimum neuromuscular stimulation. To enhance patient comfort, the stimulation output of the stimulator can be slowly "ramped up" to its full stimulation power to allow the increase in stimulation to occur at various rates to accommodate the differing characteristics of different muscle groups. A jack is provided to permit the stimulation to be controlled by an external switch operated by a clinician to coordinate stimulation of various muscle groups with voluntary muscle contraction by the patient. The jack can also be connected to a heel operated switch to stimulate muscle groups to allow certain disabled persons to walk normally. The balanced biphasic output waveform of the stimulator has a zero net DC component to minimize the possibility of skin rash developing from stimulation.

U.S. Pat. No. 4,712,558

Inventors: Geoffrey Kidd, Don Maher and Jozef Cywinski

Issued: Dec. 15, 1987

A method and apparatus are disclosed for the electrotrophic stimulation of muscle, that is, stimulation using pulses trains onto which information which will cause long-term functional and/or structural changes in the muscle tissue. This information is coded onto the interval between successive pulses of the series. Also disclosed is a method and apparatus for acquiring trophic data from motor unit action potentials U.S. Pat. No. 5,048,522

Inventor: Steven H. Petrofsky

Issued: Sep. 17, 1991

A method and apparatus are provided for electrically stimulating muscle of individuals having little or no nerve damage so the muscle can be power contracted with little pain to the individual. A therapeutic current is applied to the muscle which includes alternating desensitizing and stimulus currents. The desensitizing current is a high frequency, low amplitude current to desensitize the muscle and the stimulus current is a low frequency, high amplitude current to stimulate the muscle. The currents alternate at a point where the amplitude and slope of the two currents are substantially identical to avoid abruptions in the current. An onset failure monitor circuit is also provided to detect an increase in skim/electrode impedance indicative of possible subsequent failure of the skin-electrode connection or electrode failure.

U.S. Pat. No. 5,350,415

Inventor: Jozef Cywinski

Issued: Sep. 27, 1994

A device for trophic stimulation of muscles is provided. The device contains a pulse generation circuit that mimics the Motor Unit Action Potentials, MUAP's that are naturally generated when muscles are innervated. The invention provides the basic method for synthesizing the requisite waveform and provides the apparatus for the synthesis. Alternative pulse conditioning circuits are provided; one using a step-up transformer and one using pulse voltage multipliers. The resulting apparatus is safe, relatively painless to use and does not depend upon muscle contraction to achieve a therapeutic result.

PCT Application WO 95/33516

Inventor: Francis X. Palermo

Issued: Dec. 14, 1995

An electronic neuromuscular stimulation device (10) that is operated by a computerized electronic control unit (20). The unit (20) includes at least two and preferably four output channels to which are connected a corresponding set of electrode output cables (12). Each cable has attached a positive electrode (12D) and a negative electrode (12E) that are attached to selected areas of a patient's anatomy. The unit (20) also includes controls, indicators and circuitry that produce nerve stimulation pulses that are applied to the patient through the electrodes (12D, 12E). The nerve stimulation pulses consist of individual pulses that are arranged into pulse trains and pulse train patterns. The pulse train patterns, whose selection depends on the type of ailment being treated, includes sequential patterns, delayed overlapping patterns, triple-phase overlapping patterns, reciprocal pulse trains, and delayed sequenced "sprint interval" patterns. The overlapping patterns are particularly timed to take advantage of neurological enhancement.

U.S. Patent Number 2002/188331

Inventor: Zi-Ping Fang et al.

Issued: Dec. 12, 2002

The systems and methods provide effective neuromuscular stimulation to meet a host of different prosthetic or therapeutic objections. The systems and methods also provide convenience of operation, flexibility to meet different user-selected requirements, and transportability and ease of manipulation, that enhance the quality of life of the individual that requires chronic neuromuscular stimulation.

U.S. Pat. No. 6,701,189

Inventor: Zi-Ping Fang et al.

Issued: Mar. 2, 2004

The systems and methods provide effective neuro-stimulation to meet a host of different prosthetic or therapeutic objections. The systems and methods also provide convenience of operation, flexibility to meet different user-selected requirements, and transportability and ease of manipulation, that enhance the quality of life of the individual that requires chronic neuromuscular stimulation.

SUMMARY OF THE INVENTION

The present invention relates generally to medical treatment apparatus and more specifically, to a method and apparatus that provide pumping of venous blood and other fluids from legs by using trans-cutaneous electrical neuromuscular stimulation. The purpose of this apparatus and method is to prevent a medical condition called deep venous thrombosis (DVT) and also to reduce and/or to prevent leg and ankle swelling in persons who are motionless while standing or sitting for extended periods of time. This concerns, for example, long haul flight airline passengers or car drivers, computer operators, salesgirls, etc. The method and the device, as described in the present invention, utilize leg muscle contractions in order to obtain forced venous blood flow from legs upwards and against gravity. These contractions are caused by electro-stimulation of calf muscles and they squeeze out venous blood and other fluids from intramuscular veins and spaces and also from deep central veins in legs. This venous blood, lymph and other fluids are returned by such muscular pump to the entire circulatory system to re-enter the heart, lungs, arteries, microarterioles etc.

To obtain such muscle contractions, a special kind of electrical neuromuscular stimulation device is used. The electro-stimulation device and the method of its application are the subjects of this present invention.

The present invention utilizes short bursts of electrical impulses of high energy at a predetermined durational range wherein each burst has a modulated intensity and/or time duration associated therewith A primary object of the present invention is to provide an electro-stimulation device that will overcome the shortcomings of the prior art devices.

A secondary object of the present invention is to provide an electro-stimulation device for generating and delivering electrical impulses, which can be used to obtain strong and deep calf muscle contractions occurring simultaneously in both legs of a stimulated person.

Yet another object of the present invention is to provide an electro-stimulation device, wherein the generated electrical impulses are painless to the user.

Another object of the present invention is to provide an electro-stimulation device and method for stimulating calf muscle contractions by applying an effective predetermined set of electrical impulses.

A further object of the present invention is to provide an electro-stimulation device having predetermined sequences of impulses stored in an internal memory.

Still another object of the present invention is to provide an electro-stimulation device wherein the stored sequences of impulses are associated with a predetermined and unique condition.

Yet another object of the present invention is to provide an electro-stimulation device wherein the stored sequences are utilized for targeted treatments of medical or non-medical conditions.

A yet further object of the present invention is to provide an electro-stimulation device for painless and effective stimulation of calf muscle contractions that may be safely operated by untrained users.

Another object of the present invention is an electro-stimulation device, which utilizes a continuous train of electrical impulses at a predetermined durational range and frequency, wherein there are cyclic and short periods of modulated bursts of electric energy associated therewith.

Yet another object of the present invention is to provide an electro-stimulation method and device, wherein the generated electrical impulses include bursts of electrical energy which cause short lasting, strong and deep calf muscle contractions at a rate that approximates or is close, to a heart rate of the stimulated person.

Yet another object of the present invention is to provide an electro-stimulation method and a device, wherein the generated electrical impulses are applied by means of only two electrically conductive electrodes whereas one electrode is placed on the skin of one leg and the second electrode is placed on the skin of another leg.

Still further object of the present invention is to provide an electro-stimulation device wherein the output parameters are kept constant despite a change in power applied thereto.

A further object of the present invention is to provide an electro-stimulation device that is simple and easy to use.

A still further object of the present invention is to provide an electro-stimulation device that is economical in cost to manufacture.

Further objects of the invention will appear as the description proceeds.

The foregoing and other objects and advantages will appear from the description to follow. In the description reference is made to the accompanying drawing, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention.

In the accompanying drawing, like reference characters designate the same or similar parts throughout the several views.

To the accomplishment of the above and related objects, this invention may be embodied in the form illustrated in the accompanying drawings, attention being called to the fact, however that the drawings are illustrative only, and that changes may be made in the specific construction illustrated and described within the scope of the appended claims.

BRIEF DESCRIPTION OF THE DRAWINGS

Various other objects, features and attendant advantages of the present invention will become more fully appreciated as the same becomes better understood when considered in conjunction with the accompanying drawings, in which like reference characters designate the same or similar parts throughout the several views, and wherein.

LIST OF REFERENCE NUMERALS

Turning now descriptively to the drawings, in which similar reference characters denote similar elements throughout the several views, the Figures illustrate the electro-stimulation device of the present invention. With regard to the reference numerals used, the following numbering is used throughout the various drawing figures.

| | |
|---|---|
| 10 | the device of the present invention |
| 12 | impulse generating means |
| 14 | first output line |
| 16 | impulse conditioning means |
| 18 | first input |
| 20 | second output line |
| 22 | cable |
| 24 | electrodes |
| 26 | voltage regulator |
| 28 | power source |
| 30 | first power output |
| 32 | second power output |
| 34 | energy modulation cycles |
| 36 | energy burst period |
| 38 | energy increase phase |
| 40 | maximal energy phase |
| 42 | energy decrease phase |
| 44 | minimal energy phase |
| 46 | period of increasing contraction |
| 48 | period of decreasing contraction |
| 50 | total contraction time |
| 52 | pauses (rest) between contractions |
| 54 | input voltage shape |
| 56 | input voltage control means |
| 58 | shape conditioning means |
| 60 | output intensity control means |
| 62 | output impulse shape |
| 64 | peak-to-peak amplitude |
| 66 | positive polarity phase |
| 68 | positive peak value |
| 70 | negative polarity phase |
| 72 | negative peak value |
| 74 | impulse rise phase |
| 76 | impulse slow decay |
| 78 | impulse fall phase |
| 80 | impulse width |
| 82 | impulseBto-impulse interval |
| 84 | zero voltage line |
| 86 | step-up transformer |
| 88 | buffer |
| 90 | switching device |
| 92 | step-up DC converter |

| | | |
|---|---|---|
| 94 | digital potentiometer | |
| 96 | diodes | |
| 98 | up-down impulse control line | |

DETAILED DESCRIPTION OF THE PREFERRED EMBODIMENT

The following discussion describes in detail one embodiment of the invention and several variations of that embodiment. This discussion should not be construed, however, as limiting the invention to those particular embodiments. Practitioners skilled in the art will recognize numerous other embodiments as well. For a definition of the complete scope of the invention, the reader is directed to the appended claims.

Turning now descriptively to the drawings, in which similar reference characters denote similar elements throughout the several views, FIGS. 1 through 7 illustrate the an electrostimulation device indicated generally by the numeral 10 as well as its components and electrical impulse waveform shape.

Figure 1:
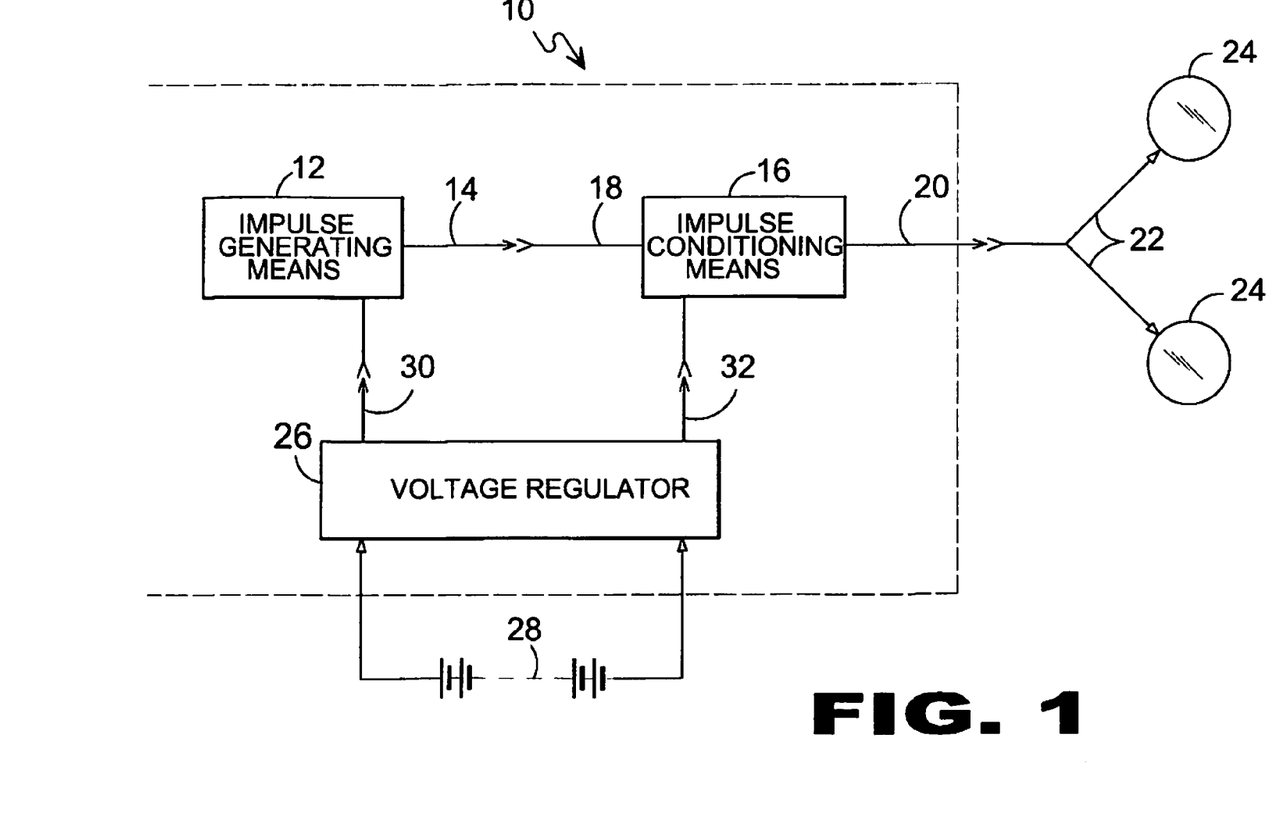
FIG. 1 is a block diagram of the electro-stimulation device of the present invention.

FIG. 1 is a block diagram of the device 10 of the present invention. The present invention discloses the device and the method of application for electrical stimulation of deep and strong leg muscle contractions. The device 10 of the present invention delivers novel waveform of electrical impulses to users by means of electrodes placed on their skin. The method of stimulation differs from the prior art stimulators. In a classical application of the prior art, in order to cause muscle contractions in both legs, the stimulation had to be delivered to separate leg muscles by means of at least four and sometimes up to twelve electrodes.

As shown on FIG. 1, the device 10 of the present invention delivers the stimulation through only two electrodes 24, whereas one electrode is applied to the left calf while the other electrode is applied to the right calf. The impulses provided by the device 10 of the present invention consist of a series of short impulses arranged in a timed pattern. These stimulation impulses also differ from prior devices by the fact that the short impulses of 5 to 200 microseconds as delivered by the device 10 are arranged in a timed pattern and replace solid impulses having much longer durations of 300 to 800 microseconds which were in prior art stimulators. Additionally, each of these short impulse generated by the device 10 of the present invention possesses a specific shape. Furthermore, these impulses include pulse-width modulation pattern as illustrated on the FIG. 2 herein.

As shown on the FIG. 1, the device 10 of the present invention includes the following components:
impulse generating means 12
impulse conditioning means 16
power source 30
voltage regulator 26
electrodes 24
cable 22 wherein a first output line 14 connects the impulse generating means 12 to a first input line 18 of an impulse conditioning means 16. A second output line 20 extends from the impulse conditioning means 16 and is coupled to the cable 22. At least one electrode 24 is positioned at an each end of the cable 22 opposite the second output line 20. The electrodes 24 are selectively positioned on the calves and removeably secured to the surface of a user's skin.

The impulse generating means 12 generates a series of electrical impulses which are arranged in a timed pattern and a modulated pattern. The impulse generating means 12 may be at least one of a mask-programmable processor or EPROM-type controllers. However, this is described for purposes of example only. In addition, the principal structures of the impulse generating means 12 can be executed in multiplicity of technologies that means hard-wired logic, custom B made logic array chips, microcontrollers or mask-programmable chips. They can all be pre-wired or preprogrammed at the factory and they do not require further adjustments when in use.

The impulse conditioning means 16 gives a specific shape to the impulses generated by the impulse generating means 12. Each impulse within the series of impulses generated has a predetermined shape. Preferably the impulses generated by the impulse generating means 12 are unidirectional and rectangular in their voltage. The impulses are output along the first output line 14 for receipt by the first input 18 of the impulse conditioning means 16. Upon the impulse conditioning means 16 receiving the impulses via the first input 18, the impulse conditioning means 16 converts every rectangular impulse into a specific shape of the waveform. The impulse conditioning means 16 may also be a stimulator output amplifier. The shaped impulses are output from the impulse conditioning means 16 to the second output line 20.

The cable 22 has two conductors and it is connected to the second output line 20 and receives the shaped impulses which pass therealong to the electrodes 24. The shaped impulses are then applied to the calf muscle of the user by means of the contact with skin.

The power source 28 which is preferably, but not limited to, a 6 or 9 volt battery supplies the power to the entire device 10. The power provided by the power supply is regulated by a voltage regulator 26 coupled thereto.

The voltage regulator 26 features two independently regulated outputs, which regulate power from the power source 28. The voltage regulator 26 provides to the impulse generating means 12 a regulated power at a level of, for example, 5 volts, through its first power output 30. Independently, the regulated power of, for example, 12 volts is also provided to the impulse conditioning means 16 by the same voltage regulator 26 from its second power output 32. This double and independently regulated output feature of the voltage regulator 26 assures no interference in function between the impulse generating means 12 and the impulse conditioning means 16.

The voltage regulator 26 assures also stable performance of the device 10 of the present invention regardless of the state of the battery discharge. For example, should the battery voltage drop from 9 volts down to 6 volts, all of the output parameters, including the shape of output current waveform and its intensity as set by the user, as well as the impulse timing patterns remain the same. However, a user may be selectively notified when such drop in the voltage occurs by a notification means (not shown) such as an LCD display or an optoelectronic display.

The voltage regulator 26 ensures additionally that the device 10 performs as intended until the voltage level from the power source 28 drops below acceptable limit or as mentioned in the above example when the 9V battery voltage drops below 6 volts, or when the battery is completely discharged. Upon complete discharge of the power source 28, the device 10 of the present invention will not produce any spurious impulses but just safely ceases to operate.

Figure 2:
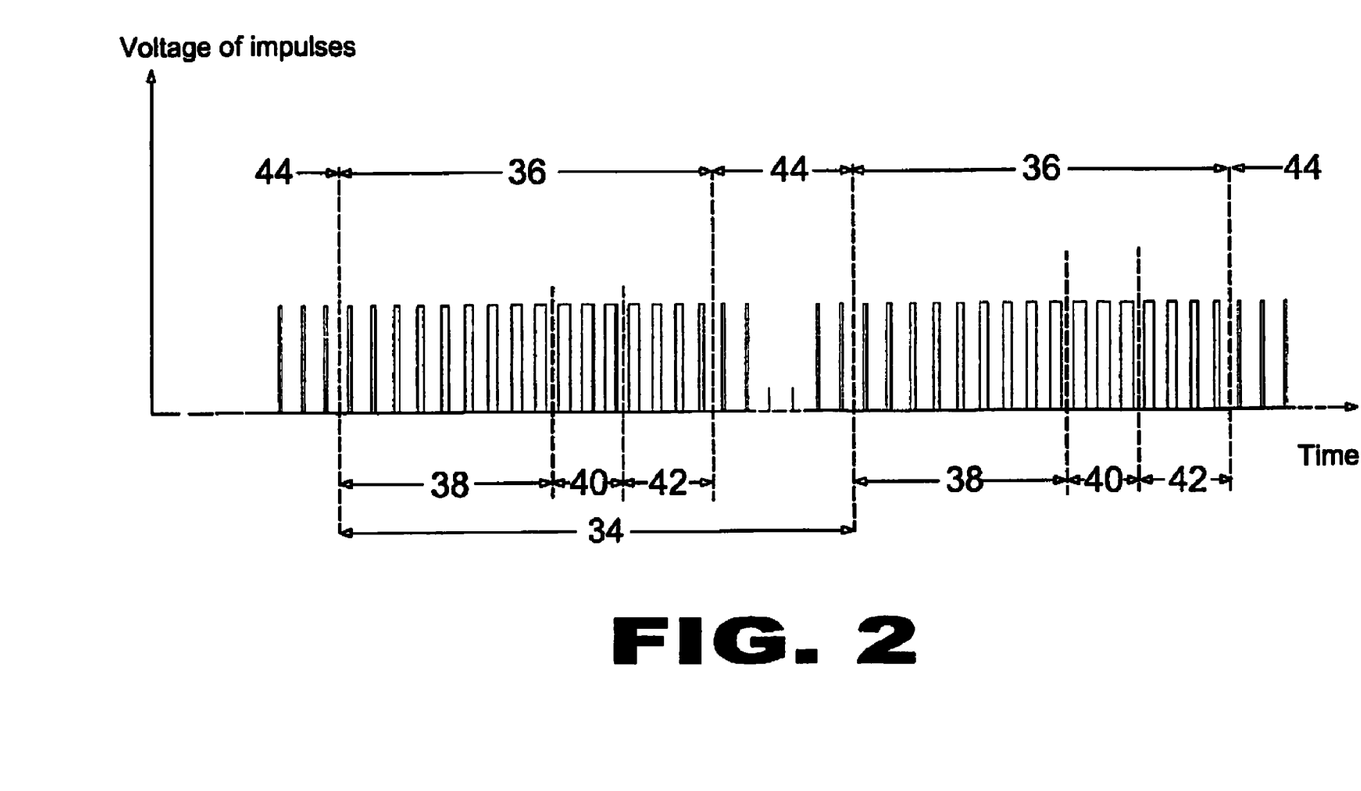
FIG. 2 is an illustrative drawing of a screen of an oscilloscope showing the impulse timing patterns of the electro-stimulation device of the present invention.

FIG. 2 illustrates an oscilloscopic output of the impulses, which are generated by the impulse generating means 12 of the present invention. Shown in FIG. 2 is an illustration of the voltage of impulses which are arranged in the timing pattern as in an exemplary embodiment of the device of the present invention. For the sake of clarity of illustration, the time-scale on the FIG. 2 was expanded and/or compressed.

FIG. 2 shows the voltage output of the impulses generated by the impulse generating means 12 and applied to the first output line 14 as discussed above with specific reference to FIG. 1. These electrical voltage impulses, which are rectangular in shape, are coming from the first output line 14 of the impulse generating means 12 and received by the first input line 18 of the impulse conditioning means 16.

As shown in FIG. 2, the impulse timing pattern is continuous with time pauses between these impulses being fixed, preferably, but not limited to, at 4 millisecond inter-pulse intervals. This is different from the prior art stimulators where the inter-pulse intervals are in the range from 1000 millisecond to approximately 15 millisecond. In addition, superimposed on these impulses there are cycles of the impulse width modulations. These impulse width modulations are appearing as energy modulation cycles having a certain time span marked with the numeral 34. Each energy modulation cycle 34 lasts for a time period marked as energy modulation cycle 34 and consists of two periods: energy burst period 36 and minimal energy phase 38. The time period of each energy modulation cycle 34 is preferably, but not limited to, to be similar to or be in complete synchrony with the heart rate of users. For simplicity, the physical embodiment device of the present claimed invention discloses the impulse timing patterns which are pre-programmed in the device memory. Their energy modulation cycle 34 repetition rate is similar to and only approximates the heart beat rate. In addition, the energy modulation cycle 34 of the impulse timing pattern in the present invention varies automatically during each treatment, for example, in several steps from 60 to 120 cycles per minute. During each and every energy modulation cycle 34 there are four distinct phases.

A first, energy increase phase 38, represents gradually increasing energy of the impulses during the energy burst period 36.

A second maximal energy phase 40, which follows, corresponds to the maximum energy of impulses provided.

A third, energy decrease phase 42 represents gradual decrease of energy of the impulses during the energy burst period 36.

A fourth minimal energy phase 44, which follows, represents a minimal level of energy of the impulses in the entire energy modulation cycle 34. The impulses received in the minimal energy phase 44 are carrying too little energy and do not cause contractions of muscles but are delivered in between the muscle contractions. Each phase will be discussed in greater detail hereinbelow.

In the prior art, all stimulating impulse capable of causing tetanic muscle contractions were of long time duration and of high energy, so they could not be applied continuously. They required long silent periods between these tetanic contractions in order not to fatigue or eventually damage the muscles. As illustrated on the FIG. 2, the impulse timing pattern of the device 10 of the present invention replaces each individual impulse or tetanic modality of the prior art with a continuous series of much shorter impulses, which are occurring with cyclically modulated duration times of each impulse As mentioned above, the series of stimulating impulses, which are subject of this invention, consists of four phases, which are now described in detail, below.

The first, energy increase phase 38 of the impulse series consists of several narrow impulses appearing at a fixed frequency of, for example, 250 Hertz and are provided with gradually increasing energy. This increase preferably is accomplished, but not limited to, by the modulation of the impulse width (duration) in an exponential fashion by the impulse generating means 12 or by the modulation of impulse amplitude by the specific preprogrammed interaction between impulse generating means 12 and impulse conditioning means 16. For example, in the physical embodiment of the device of the present invention this variability of impulse width is in the range of from 26 to 240 microseconds and this energy increase phase 38 consists of 30 impulses. The gradual increase of energy prevent rapid onset and a startling effect of a single stimulation impulse or a user perceived electric shock during an onset of tetanic contractions.

The second, maximal energy phase 40 represents steady impulse energy phase and, for example, in the physical embodiment of the device of the present invention it consists of three impulses of a duration time width of 240 microseconds, appearing at, but not limited to, a fixed frequency of 250 Hertz, while each of the impulses has maximum energy. This maximum energy of these very few impulses penetrates deep enough so as to allow for deep and painless muscle contraction of the calf muscles.

The third, energy decrease phase 42 consists of several impulses appearing at a fixed, but not limited to, frequency of, 250 Hertz with gradually diminishing impulse energy (time duration of impulses). Preferably, for example, as in the physical embodiment of the device of the present invention this decrease in impulse energy occurs during eight impulses and has character of linear decrease while changing the impulse width in a range from 200 down to 26 microseconds.

The fourth, minimal energy phase 44 is pre- or inter-contraction period during which there are several impulses of minimal duration and constant but small energy with time duration of each impulse ranging from for example, 5 to 40 microseconds appearing at fixed frequency of, for example, but not limited to, 250 Hertz. The impulses received during this fourth phase 44 carry too little energy to cause contractions of muscles but are timed to be in between the contractions and they serve an additional role of electro-anesthetizing the pain receptors in the skin in order to provide painless calf muscle contractions, during subsequent phases of the cycle and the energy modulation cycles 34, which follow. In the exemplary physical embodiment of the present invention these minimal energy phases change during the treatment and last from 400 to 900 milliseconds.

The impulse time pattern output by the device 10 of the present invention and discussed hereinabove can be used differently for different applications. The difference can be in the frequency of repetition of individual impulses in the series, the total number of impulses in the series, their energy modulation patterns and their time intervals between the impulses of maximal energy. This allows the impulses of the present invention to treat medical and non-medical conditions such as, but not limited to, muscle recovery after exercise, reduction of joint swelling, and prevention of deep venous thrombosis and leg swelling such as when a user is on a long flight or immobilized.

Figure 3:
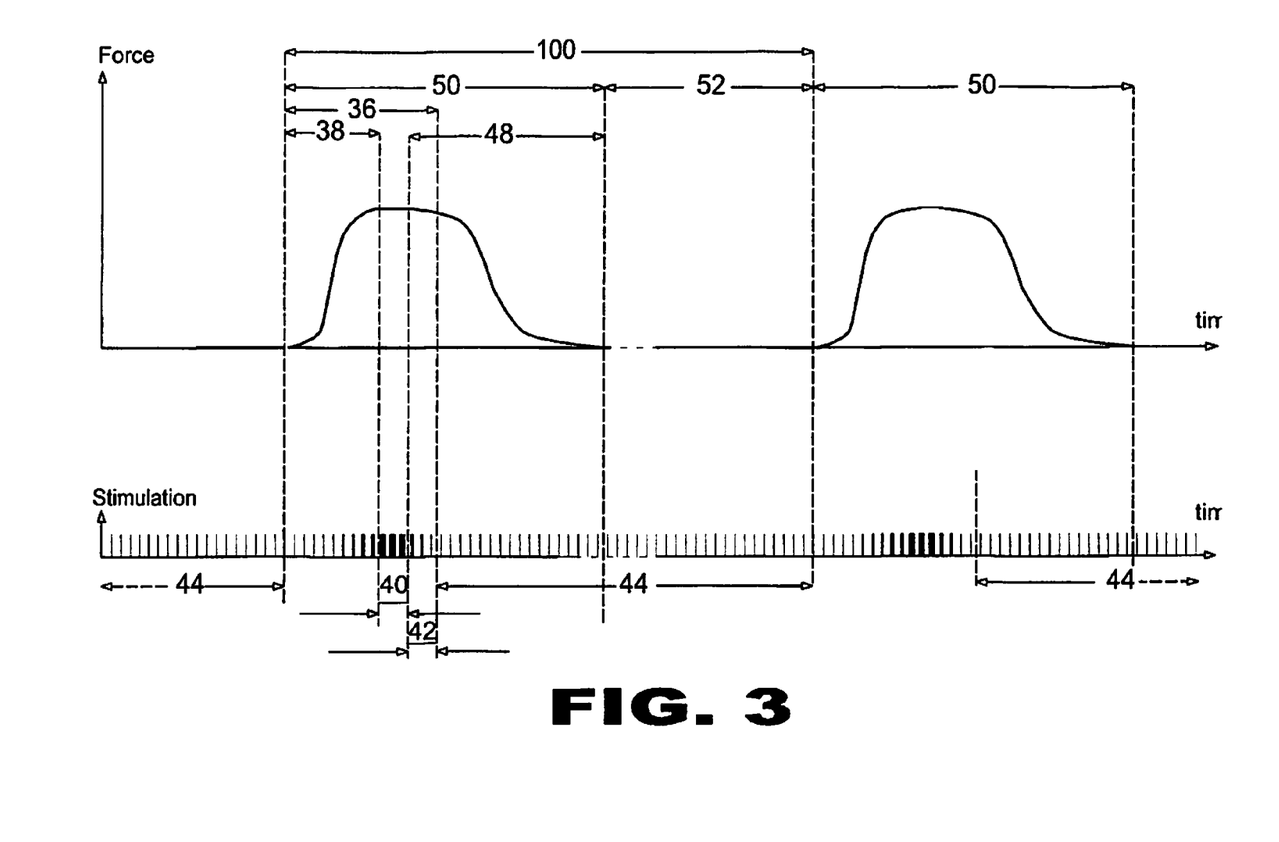
FIG. 3 is a graphical representation of calf muscle contraction force over time during the application of an impulse timing pattern of the electro-stimulation device of the present invention.

FIG. 3 is a graphical representation of muscle force over time during the application of an impulse timing pattern of the electro-stimulation device of the present invention. Specifically, the graphs on the FIG. 3 show the relations between the stimulation impulses and the muscle contractile force. The upper graph shows the force of the muscle contraction, which is synchronous with, and is caused by the stimulation with impulses having the timing pattern generated by the device of the present invention. The stimulation timing pattern is shown on a bottom trace in FIG. 3. The muscle contractions as represented on the top trace occur repetitively in synchrony with the energy modulation cycles 34. Their repetition time periods are changing automatically during a treatment in a range from 1 second to 0.5 second in the exemplary physical embodiment of the device 10 of the present invention. When the energy of stimulating impulses gradually increases during the energy increase phase 38, there is a corresponding and rapid increase of a muscle contraction marked by the numeral 46. Then, after achieving maximal muscle contraction, the force of muscle is followed by the period of decreasing contraction 48.

Because of the nature of the muscle each muscle total contraction time 50 lasts longer than the impulse energy burst period 36. The force during the 48 lasts longer and not only during the period of impulse energy decrease phase 42, but also during the first part of the phase of minimal energy phase 42. This is a natural phenomenon and occurs in spite of that the impulse energy during this period of minimal energy phase 42 is too small to cause active contraction of the muscle. For example, while the impulse maximal energy phase 40 is in a range of 0.01 to 0.02 seconds, the entire calf muscle total contraction time 50 may last for up to 0.3 seconds. These long lasting contractions of calf muscles are effectively squeezing out and pumping the venous blood and other fluids from leg veins back into central circulatory system.

A graphical representation of the embodiment of the device 10 described herein with specific reference to FIG. 2 wherein the targeted muscle is a leg muscle. Preferably, FIG. 3 shows the muscle contraction of stimulated calf muscles in a leg, which are used for venous blood and other fluid pumping and reduction of leg swelling in order to prevent or treat medical conditions called venous thrombosis. However, this condition is described for purposes of example only and the device may be used to treat other condition related to the muscular-skeletal system.

The graph in FIG. 3 shows the timing pattern of the device 10 having narrow impulses of modulated energy. However, this is described for purpose of example only and the impulse generating means 12 may generate the impulses having any width or a modulated impulse width thereof.

Figure 4:
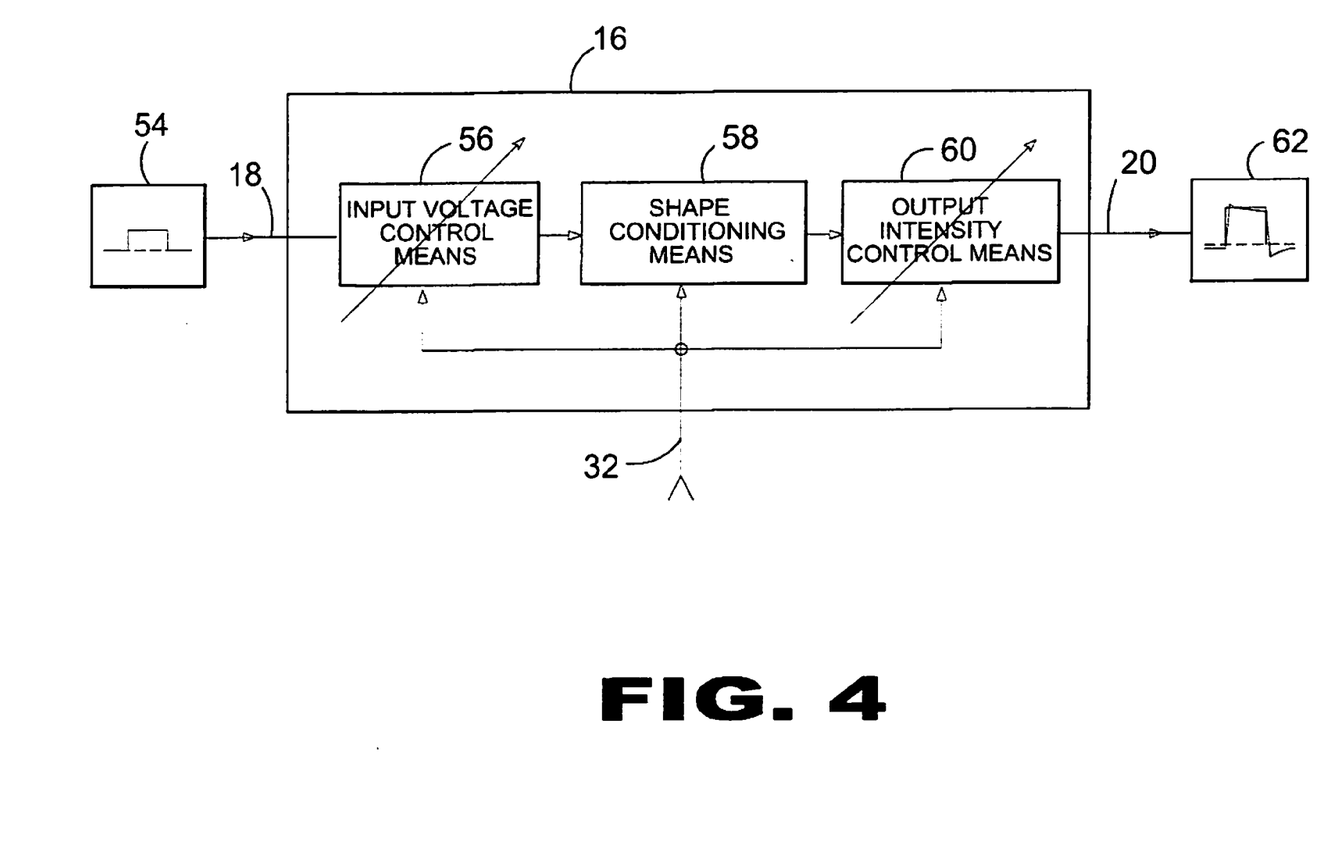
FIG. 4 is a block diagram of the impulse conditioning means, which are a part of the electro-stimulation device of the present invention.

FIG. 4 is a block diagram of the impulse conditioning means 16 which are a part of the electro-stimulation device 10 of the present invention and are otherwise known as the stimulator output circuit. The impulse generating means 12 generates a series of electrical impulses arranged in a timed pattern and a modulated pattern. Each impulse within the series of impulses generated has a predetermined shape. Preferably the impulses generated by the impulse generating means 12 are unidirectional and rectangular in shape of their voltage waveform. The impulses are output along the first output 14 for receipt by the first input 18 of the impulse conditioning means 16. Upon the impulse conditioning means 16 receiving the impulses via the first input 18, the impulse conditioning means 16 convert every rectangular unidirectional impulse into a specific shape of the current waveform which is bi-directional as shown later in the FIG. 5 herein. The shaped impulses are output from the impulse conditioning means 16 to the second output 20.

The impulse conditioning means 16 include three distinct components:
input voltage control means 56 which are coupled to the shape conditioning means 58, which are further coupled to an
output intensity control means 60.

The first input 18 is coupled to the impulse input voltage control means 56 of the impulse conditioning means 16 and the second output 20 is coupled to the impulse output intensity control means 60.

The time course of the shape of voltage entering the impulse conditioning means 16 via the first input 18 is depicted in graphical form and labeled as input voltage shape 54. Upon the input voltage shape 54 entering the impulse conditioning means 16, the voltage waveform output therefrom is represented in graphical form as the output impulse shape 62. The first input 18 of the impulse conditioning means 16 is connected to the second output line 20 of the impulse generating means 12 as shown before in FIG. 1. The rectangular impulses illustrated as input voltage shape 54 are received by the input voltage control means 56. Within the impulse conditioning means 16 there are also the output intensity control means 60 which include at least one of digital and/or analog potentiometers. The third component of the impulse conditioning means 16 namely the shape conditioning means 58 convert the rectangular input voltage shape 54 impulses in their timing patterns coming from the impulse generating means 12 into a specific predetermined output impulse shape 62. This character of the output impulse shape 62 will be discussed hereinafter with specific reference to FIG. 5.

Upon receiving the rectangular input voltage shape 54 impulse, the input voltage control means 56 within the impulse conditioning means 16 controls the voltage of the impulse and the shape conditioning means 58 adjust the shape and condition of the output impulse. Finally, the impulse output intensity control means 60 adjusts the intensity such that the resultant output impulse shape 62 is in the predetermined shape and adequate intensity to effectively cause painless calf muscle contractions.

Figure 5:
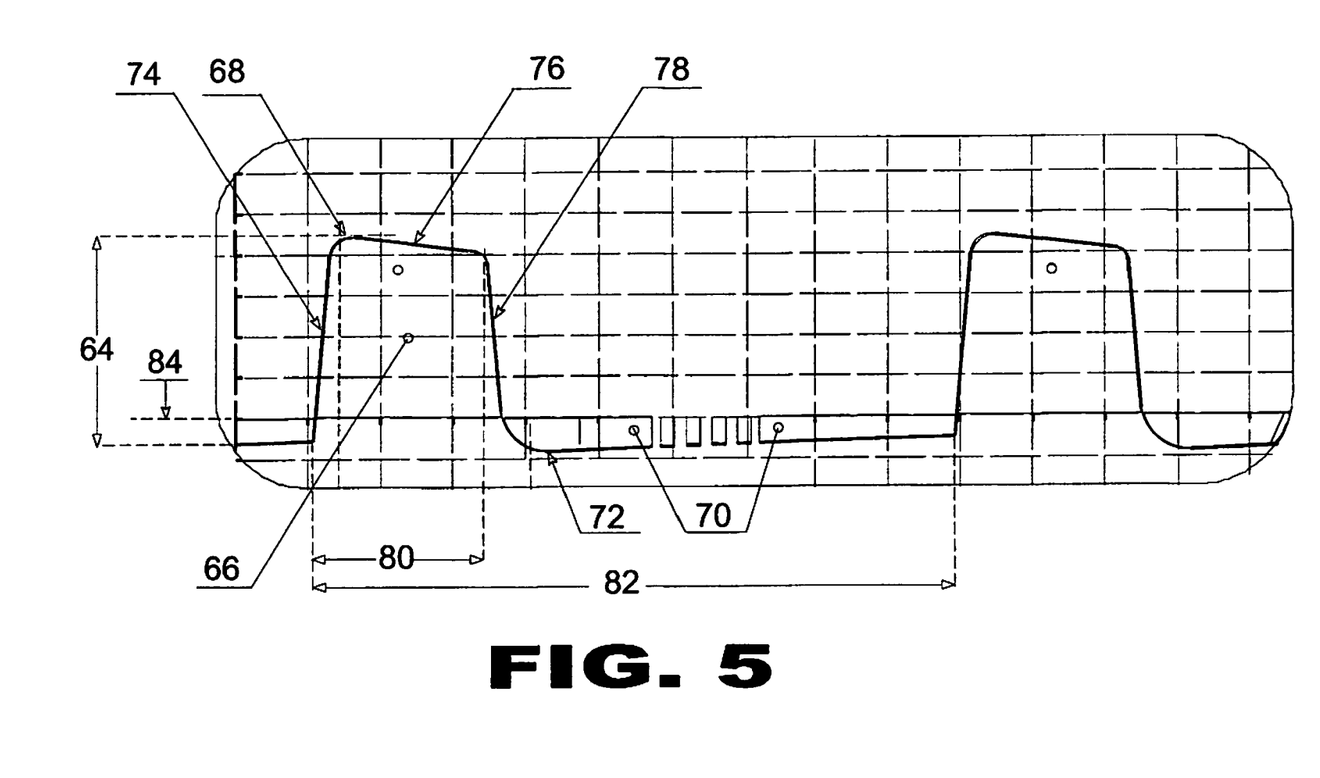
FIG. 5 is an illustrative view of a screen of an oscilloscope showing the shape of the single impulse waveform provided by impulse conditioning means of the electro-stimulation device of the present invention.

FIG. 5 is an illustrative view of an oscilloscope screen showing the details of the voltage waveform of the output impulse shape 62 of the individual impulses provided by the electro-stimulation device 10 of the present invention. For a clarity of illustration, the time and voltage intensity scales on this FIG. 5 has been compressed and/or expanded.

The waveform shown in FIG. 5 is an exemplary depiction of the two consecutive and predetermined output impulse shapes 62 as shown and described hereinabove with specific reference to the FIG. 4. In the example illustrated herein, the waveform shown is output at the second output 20 of the impulse conditioning means 16, which is further transmitted through the cable 22 to the resistive load of 500 ohms which is connected in place of the electrodes 24 for the purpose of this oscilloscope recording. The vertical axis of the graph grid as shown in FIG. 5 represents increasing increments of 10 volts, wherein the horizontal axis represents increasing time having increments of 10 microseconds. As illustrated on the FIG. 5, the peak-to-peak amplitude 64 value of the impulse voltage during this exemplary impulse is approximately 50V, which corresponds to 100 mA current intensity, while the impulse duration time is approx. 25 microseconds.

The individual impulse waveform illustrated as the output impulse shape 62 includes two phases, a positive polarity phase 66, which is above zero voltage line 84 and a negative polarity phase 70, which is below zero voltage line 84. The current flowing in the second output line 20 connected to the resistive load during the positive polarity phase 66 flows in opposite direction from the current flowing in the negative polarity phase 70. It is important to have the opposite polarity as shown by the negative polarity phase 70 because symmetry of electrical charges flow between the phases is desirable. In the device of the present invention, the net flow of electrical energy of these two phases balances each other in a way that the electrical charges of the positive polarity phase 66 and that of the negative polarity phase 70 compensate each other as being in opposite directions from the zero voltage line 84, and their integrated sum equals zero. Having such symmetry between the charge of phases results in the prevention of net DC current flowing through the electrodes to the user thereby causing the user discomfort and/or painful skin reaction. Furthermore, the symmetry and the character of this output impulse shape 62 allows for stimulation output by the device 10 of the present invention to cause very strong but painless contractions of calf muscles.

In addition to the symmetry, the output impulse shape 62 has following features which determine the unique character of the stimulating impulse. As shown in FIG. 5 the impulse rise phase 74 shows the intensity of the current rising quickly to reach a predetermined positive peak value 68. Upon reaching the positive peak value 68 the current intensity starts impulse slow decay phase 76. After the time period corresponding to the impulse width 80, the impulse fall phase 78 begins whereas the current intensity drops quickly to a level of the negative peak value 72, which is below zero voltage line 84. The impulse rise phase 74 occurs in a time ranging substantially between 0.5 and 4 microseconds, depending on the electronic components comprising of the device 10. The time duration of the impulse slow decay phase 76 depends on impulse width 80 and ranges between 25 and 200 microseconds whereas the drop in intensity also varies with the impulse width 80 and stays in a range of 1% to 15% of the predetermined positive peak value 68. The impulse fall phase 78 lasts for twice as long time as the impulse rise phase 74 mentioned above and is followed by a negative polarity phase 70 featuring low current intensity and lasting for a longer time as compared to the individual impulse durational time. The duration of the negative polarity phase 70 is in fact, up to 160 times longer then the impulse width 80, which is 25 microseconds as illustrated in example herein. The time of the negative polarity phase 70 is close to the impulse-to-impulse interval 82, of 4000 microseconds, as illustrated in example herein. Therefore in this illustrated example of the impulse width 80 being set at 25 microseconds, the negative peak value 72 of current intensity is 160 times smaller than the 100 mA value of the positive peak value 68 and equals to 0.625 mA. In case of a different impulse width 80, for example being set at 200 microseconds, the peak current intensity of the negative polarity phase 70 will be only 20 times smaller than the 100 mA current intensity during the positive polarity phase 66 and equal to 5 mA. For a clarity of illustration, the negative polarity phase 70 is not drawn to scale on the FIG. 5. The ranges of times are only affected by the electronic components inside the device 10 but not affected by the electrodes 24 or pads used to cover the electrodes 24.

Figure 6:
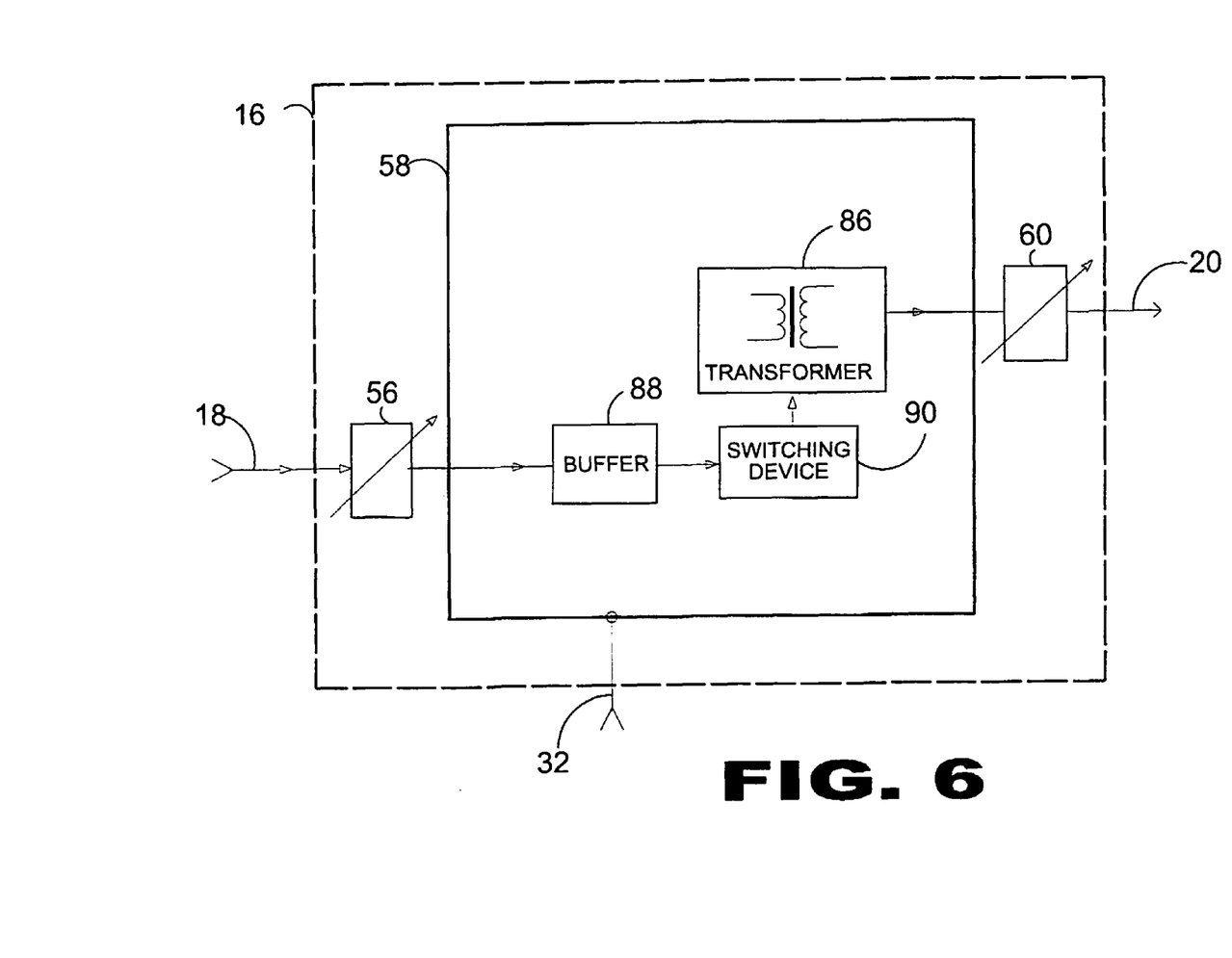
FIG. 6 is a block electrical diagram of an exemplary embodiment of the impulse conditioning means of the electro-stimulation device of the present invention.

FIG. 6 is a block electrical circuit diagram of the example of the physical embodiment of the impulse conditioning means 16 contained within the device 10 according to the present invention. Shown in FIG. 6 are components and their connections of the impulse conditioning means 16 described hereinabove with specific reference to FIG. 4. In this example, the impulse conditioning means 16 includes a step-up transformer 86 coupled to both a power switching device 90 and a buffer 88. The output shape conditioning means 58 is coupled between the input voltage control means 56 and the output intensity control means 60. The step-up transformer 86 steps up the voltage at a ratio of substantially 1:5 and is driven by the power switching device 90. The power switching device 90 is controlled by impulses received by the first input 18 from the impulse generating means 12. Thereafter, the output intensity control means 60 control the intensity of the impulses output from the impulse conditioning means 16 via an analog potentiometer connected to a secondary winding of the step-up transformer 86 or by a digital potentiometer connected via the buffer 88 at the primary winding of the step-up transformer 86. The performance and applicability of the circuit described above depend on the design of the transformer and matching the characteristic load thereto of the electrodes placed over the user's skin.

Figure 7:
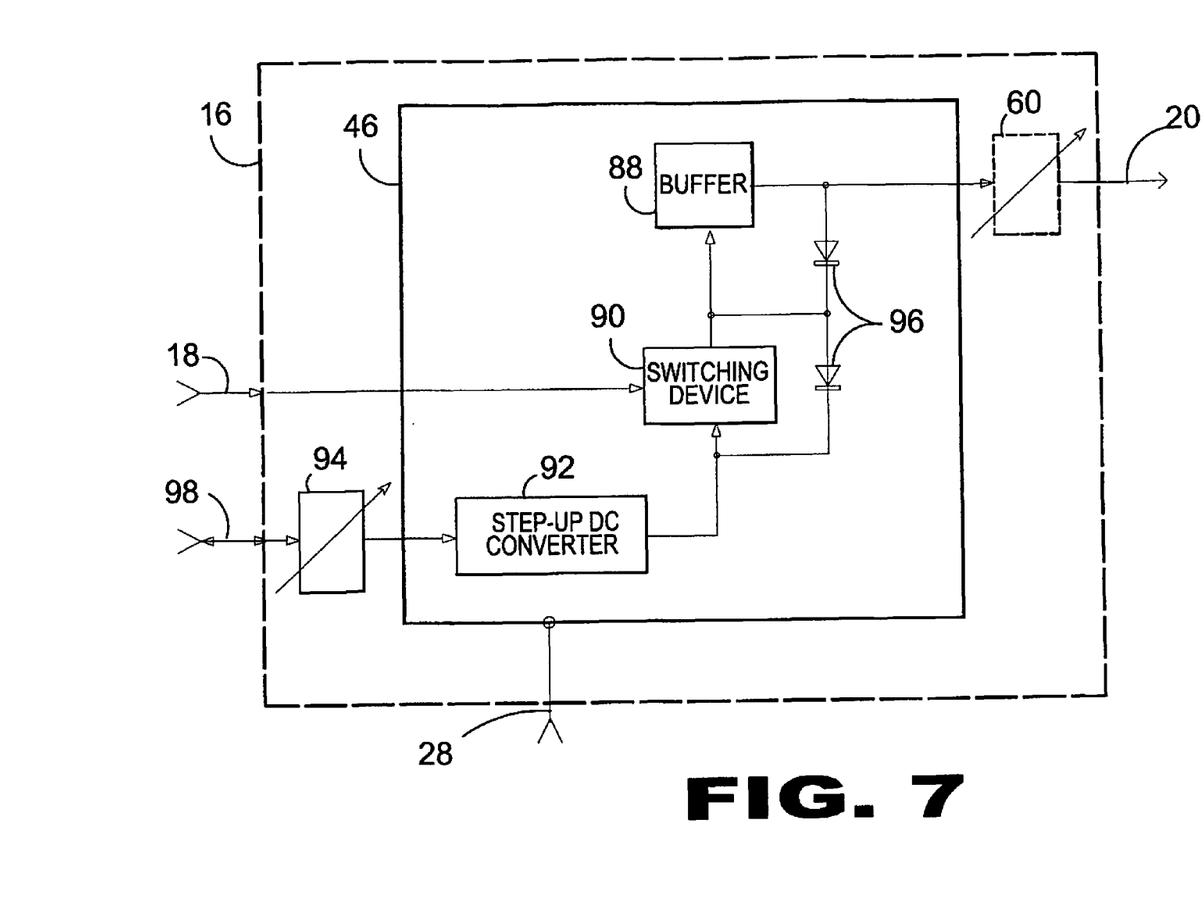
FIG. 7 is a block electrical diagram of an alternate embodiment of impulse conditioning means of the electro stimulation device of the present invention.

FIG. 7 is a block electrical diagram of an alternate embodiment of the electro stimulation device of the present invention. Shown herein is an alternate embodiment of the impulse conditioning means 16 using a transformer-less output stage. The impulse conditioning means 16 comprises a step-up DC converter 92 having a digital potentiometer 94 coupled thereto. The step-up DC converter 92 is further connected to the power switching device 90 having diodes 96 connected thereto. An amplifier buffer 88 is serially connected to the power switching device 90 and the second output 20 extends therefrom.

The output voltage presented at the second output 20 from the he impulse conditioning means 16 is controlled by the digital potentiometer 94, which in turn is controlled by the pushbutton up-down switches (not shown) which are connected to the impulse generating means 12 via the up-down control line 98. The digital potentiometer 94 selectively sets the voltage of the step-up DC converter 92 to be delivered to the power switching device 90. The power switching device 90 applies the stepped up voltage to the received impulse via the first output line 14 from the impulse generating means 12. Thereafter the impulse is received by the buffer 88 and is output via the second output 20 for transmission through the cable 22 and application to the user via the electrodes 24. As discussed above with specific reference to FIG. 6, the performance of this transformer-less circuit depends on the careful matching of its characteristics to the load conditions between the electrodes 24.

The output signals from the impulse generating means 12 and made available at its' first output line 14, are used to trigger the impulse conditioning means 16. The conditioning of output impulses is necessary in order to be compatible with the requirements for the stimulation through the skin by means of electrodes 24 to the underlying calf and other muscles. This device 10 for painless stimulation of calf muscle contractions has no need for user-accessible adjustments except for the intensity control of stimulation. Due to the device design of the impulse conditioning means 16 and the impulse timing sequences produced by the impulse generating means 12, most of the electrical parameters like impulse energy, duration and frequency, are outside and beyond of pain receptors maximum sensitivity range. Therefore the device as in this instant invention causes strong contractions of the calf muscles, which produce desired therapeutic results with no pain sensation to users. The therapeutic results are noticed in relatively shorter times than with other methods, with added patients convenience and simplicity of use.

Additionally, the electrostimulation device 10 of the present invention may include a memory unit for storing a plurality of different timing patterns for future broadening the use of the device in treating a plurality of medical and non-medical conditions.

It will be understood that each of the elements described above, or two or more together may also find a useful application in other types of methods differing from the type described above.

While certain novel features of this invention have been shown and described are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A device for providing venous blood pumping from the legs by electric stimulation for treatment of medical and non-medical conditions comprising:
   a) means for generating unidirectional electrical impulses shaped according to a pre-stored timing pattern;
   b) means for conditioning said shaped impulses by converting each said shaped impulse into a bidirectional preselected shaped output pulse;
   c) means for applying said output impulses directly to calf muscles of a user by using only a single electrode on the skin of each leg of the user capable off causing deep and strong painless contraction of a user's leg muscles, each output impulse comprising a positive phase having a current flowing in a first direction and a negative phase having a current flowing in a direction opposite said first direction, said positive and negative phases comprising an energy modulation cycle, the integrated sum of positive and negative phases of each energy modulation cycle being zero to prevent net DC current flowing through the electrodes which would cause discomfort and/or painful skin reaction, wherein said device consists of only two electrodes; and
   d) wherein said means for generating said shaped impulses includes a continuous train of very short electrical impulses and rhythmic periods of modulated bursts of energy superimposed on top of said continuous train of electrical impulses.

2. The device as recited in claim 1, wherein said pre-stored timing pattern controls said impulse generating means to generate a polygonal shaped impulse.

3. The device as recited in claim 2, wherein said polygonal shaped impulse is at least one of a rectangular shaped impulse, a square shaped impulse, a triangular shaped impulse and a trapezoidal shaped impulse.

4. The device as recited in claim 1, wherein said prestored timing pattern comprises:
   a) a first phase for increasing energy of said shaped impulse;
   b) a second phase following said first phase, wherein said shaped impulse has a maximum amount of energy;
   c) a third phase following said second phase wherein energy of said shaped impulse is decreasing; and
   d) a fourth phase following said third phase and immediately preceding said first phase, wherein said shaped impulse has a minimum level of energy.

5. The device as recited in claim 4, wherein the time period of each energy modulation cycle is in synchrony with the heart rate of the user.

6. The device as recited in claim 4, wherein said positive phase comprises:
   a) a first stage for an increase of current intensity in a time ranging between about 0.5 and 4 microseconds;
   b) a second stage representing said current intensity reaching a peak value and decaying in a time ranging between about 25 and 200 microseconds; and;
   c) a third stage wherein said current intensity is reduced exponentially until said current intensity is below a zero value and has a time duration of about twice as tong as the first stage.

7. The device as recited in claim 6, wherein current intensity rises in said first stage at a time value (T) ranging substantially between 0.5 and 4 microseconds.

8. The device as recited in claim 7, wherein current intensity decreases in said third stage at a time value (T) ranging substantially between 5 and 200 microseconds.

9. The device as recited in claim 8, further comprising a power source and a voltage regulator coupled thereto, wherein said voltage regulator has two independently regulated outputs, providing said conditioning means with about twice the voltage of said impulse generating means and assuring no interference in function between said impulse generating means and said conditioning means.

10. A method for causing muscle contractions in calf muscles of a user using an electro-stimulation device comprising the steps of:
    a) generating shaped electrical impulses;
    b) conditioning the generated shaped electrical impulses so that each conditioned impulse comprises a positive phase having a current flowing in a first direction and a negative phase having a current flowing in an opposite direction, said positive and negative phases comprising an energy modulation cycle, the integrated sum of positive and negative phases of each energy modulation cycle being zero so that there is no net DC current flow; and
    c) applying said conditioned shaped impulse to a user using only one electrode on the skin of each leg of the user causing deep and strong painless muscle contractions in calves of both legs and whereby said no net DC current flow through the electrodes which would avoid discomfort and/or painful skin reaction in the user; and
    d) wherein the stimulation utilizes a continuous train of very short electrical impulses and rhythmic periods of modulated bursts of energy superimposed on top of said continuous train of electrical impulses.

11. The method of claim 10, wherein said method employs only two electrodes.

12. The method of claim 10, wherein said shaped electrical impulses have a slow decay positioned between an impulse rise phase and an impulse fall phase.

13. The Method of claim 12, wherein said impulse rise phase being longer than said impulse fall phase.

14. The method of claim 10, wherein said deep and strong painless muscle contractions are tetanic contractions.

15. A device for providing venous blood pumping from the legs by electric stimulation for treatment of medical and non-medical conditions comprising:
    a) means for generating unidirectional electrical impulses shaped according to a pre-stored timing pattern;
    b) means for conditioning said shaped impulses by converting each said shaped impulse into a bidirectional preselected shaped output pulse;
    c) means for applying said output impulses directly to calf muscles of a user by using only a single electrode on the skin of each leg of the user causing deep and pathless contractions of a user's leg muscles, each output impulse comprising a positive phase having a current flowing in a first direction and a negative phase having a current flowing in a direction opposite said first direction, said positive and negative phases comprising an energy modulation cycle, the integrated sum of positive and negative phases of each energy modulation cycle being zero to prevent net DC current flowing through the electrodes which would cause discomfort and/or painful skin reaction, wherein said device consists of only two electrodes; and d) wherein said electrical impulses have a slow decay positioned between an impulse rise phase and an impulse fall phase, said impulse rise phase being longer than said impulse fall phase; and e) wherein said means for generating said shaped impulses includes a continuous train of very short electrical impulses and rhythmic periods of modulated bursts of energy superimposed on top of said continuous train of electrical impulses.

\* \* \* \* \*